United States Patent [19]

Cooper

[11] Patent Number: 4,981,795
[45] Date of Patent: Jan. 1, 1991

[54] MICROORGANISM FOR PREPARATION OF CONIFERYLALDEHYDE

[75] Inventor: Bryan Cooper, Mannheim, Fed. Rep. of Germany

[73] Assignee: BASF Aktiengesellschaft, Ludwigshafen, Fed. Rep. of Germany

[21] Appl. No.: 362,678

[22] Filed: Jun. 7, 1989

Related U.S. Application Data

[63] Continuation of Ser. No. 7/012,495, Feb. 9, 1987.

[30] Foreign Application Priority Data

Feb. 15, 1986 [DE] Fed. Rep. of Germany ....... 3604874

[51] Int. Cl.$^5$ .......................... C12R 1/06; C12P 7/24; C12P 1/04

[52] U.S. Cl. ................................. 435/147; 435/170; 435/830

[58] Field of Search ........................ 435/147, 170, 830

[56] References Cited

PUBLICATIONS

Yamada et al., Appl. Env. Microbiol. 33(4): 771–776 (1977).
Tadasa, Agric. Biol. Chem. 41(6): 925–929(1977).
Tadasa et al., Agric. Biol. Chem. 47(11): 2639–2640(1983).

Primary Examiner—Robert A. Wax
Assistant Examiner—Stephanie W. Zitomer
Attorney, Agent, or Firm—Oblon, Spivak, McClelland, Maier & Neustadt

[57] ABSTRACT

Novel microorganisms can be used to convert n-eugenol to coniferylaldehyde.

1 Claim, No Drawings

MICROORGANISM FOR PREPARATION OF CONIFERYLALDEHYDE

This is a continuation, of application Ser. No. 07/012,495, filed on Feb. 9, 1987.

The present invention relates to a process for the preparation of coniferylaldehyde, and microorganisms which are suitable for this purpose.

Coniferylaldehyde is an intermediate for the preparation of vanillin, a flavoring widely used in the food industry. The aldehyde can be readily converted to vanillin by heating in the presence of sodium hydroxide solution (Acta Chem. Scand. 3 (1949), 86).

It has already been stated that n-eugenol (A) can be subjected to oxidative degradation via ferulic acid (B) using microorganisms (Agric. Biol. Chem. 41 (1977), 925). In this degradation, vanillic acid (D) is always formed in considerable amounts in addition to vanillin (C):

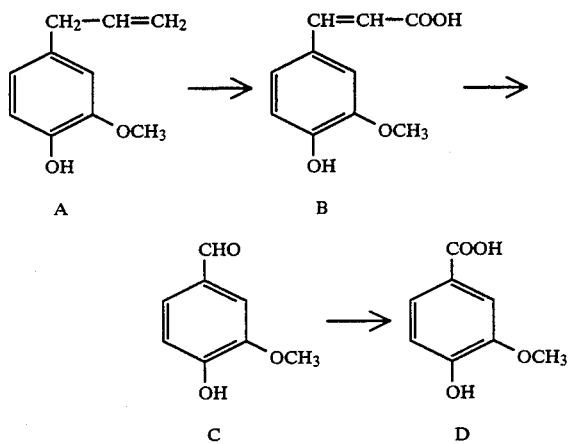

However, the microorganisms required for this reaction are not obtainable, so that the process cannot be carried out.

In Agric. Biol. Chem. 47 (1983), 2639 it is furthermore stated that n-eugenol can be converted to B via coniferylaldehyde (E).

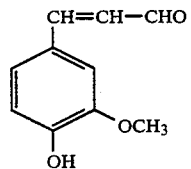

This process too cannot be repeated since the microorganism used is not available.

We have found microorganisms which are capable of converting n-eugenol to coniferylaldehyde.

The present invention relates to the bacterium *Arthrobacter globiformis* DSM 3597 and its mutants which convert n-eugenol to coniferylaldehyde.

From a taxonomic point of view, *Arthrobacter globiformis* DSM 3597 can be described as follows:

1. Form of the cells (liquid culture in nutrient broth observed at 20° C. and 250 rpm):

Rods measuring 0.5–0.8×1–5 μm. During growth, irregular shapes occur which may be substantially larger. Toward the end of growth, predominantly coccoid forms (0.5–1.0 μm diameter) occur and are preferentially associated in large clusters.

2. Mobility: not mobile.
3. Spores: none observed.
4. Gram staining: positive in all growth phases.
5. Growth on minimal medium +1% of glycerol: positive in 3 to 6 days.

Composition of the minimal medium:

0.5% of ammonium sulfate, 0.15% of potassium dihydrogen phosphate, 0.36% of dipotassium hydrogen phosphate, 0.05% of magnesium sulfate 0.7 hydrate, 0.005% of manganese sulfate 0.1 hydrate, 0.2% of trace element solution and 1.8% of agar.

Composition of the trace element solution: 200 mg/l of iron (II) sulfate monohydrate, 10 mg/l of zinc (II) sulfate 0.4 hydrate, 3 mg/l of maganese (II) sulfate 0.4 hydrate, 30 mg/l of boric acid, 20 mg/l of cobalt (II) chloride 0.6 hydrate, 1 mg/l of copper (II) chloride 0.2 hydrate, 2 mg/l of nickel (II) chloride 0.6 hydrate, 3 mg/l of sodium molybdate 0.2 hydrate and 500 mg/l of EDTA in distilled water.

6. Vitamin requirement: none.

Stimulation of growth on glycerol minimal medium by the addition of 0.1 mg/l of biotin: very pronounced.

7. Colony morphology: flat, shiny, predominantly pale yellow colonies. White variants occur spontaneously.

8. Growth on calf serum/peptone/tellurite agar (37° C.): small, black colonies within 12 days.

9. Anaerobic growth: no growth within 8 days with 1% of D-glucose as the carbon source in nutrient broth medium.

10. Utilizable nitrogen sources: ammonium sulfate, potassium nitrate, urea and, after an initiation phase, elemental nitrogen.

11. Temperature range: growth at 22° C. and 37° C. Optimum: 28° C.

12. C sources: growth on the following C sources (1 g/l), tested in minimal medium enriched with 0.1 mg/l of biotin:

| | |
|---|---|
| Glycerol: | positive |
| Tyramine: | positive |
| Uric acid: | positive |
| 4-hydroxybenzoic acid | positive |
| 3,4-dihydroxybenzoic acid | positive |
| 3-hydroxybenzoic acid: | positive |
| D-xylose: | positive |
| Melezitose: | positive |
| D-glucuronic acid: | positive |
| D-glucosamine: | positive |
| Myo-inositol: | positive |
| 2-oxoglutaric acid: | positive |

13. Catalase: positive

Suitable mutants of *Arthrobacter globiformis* DSM 3597 are obtained by spontaneous or induced mutation. For example, the mutagenic treatment can be effected by exposure to UV radiation or by treatment with mutagenic substances, such as N-methyl-N'-nitro-N-nitrosoguanidine (MNNG). The mutants thus obtained are then selected according to their ability to convert n-eugenol to coniferylaldehyde, without further changing the coniferylaldehyde.

The present invention furthermore relates to a process for the preparation of coniferylaldehyde, wherein suitable mutants of the strain *Arthrobacter globiformis* DSM 3597 are cultivated in the presence of n-eugenol.

To carry out the novel process, suitable mutants of the strain *Arthrobacter globiformis* DSM 3597 are transferred to an n-eugenol-containing nutrient medium and incubated therein, preferably at pH 6-8 and at 22°-37° C. Fermentation can be carried out continuously or batchwise.

The cells of the strain used, which may also be employed in the form of quiescent cells which are not growing, are allowed to act directly on the substrate. Any known incubation method may be used, although fermenters in the form of deep, aerated and stirred tanks are particularly preferred. Very good results are obtained by incubating the liquid nutrient medium.

The choice of nutrient medium for cultivating the microorganism is not critical. Particularly suitable nutrient media are those which contain carbon sources, nitrogen sources, inorganic salts and, if required, small amounts of trace elements and vitamins. Suitable nitrogen sources are inorganic or organic nitrogen compounds or materials which contain these compounds. Examples are ammonium salts, nitrates, cornsteep liquor, brewers yeast autolysate, soybean meal, wheat gluten, yeast extract, yeast, urea and potatoe protein. Examples of suitable carbon sources, in addition to the n-eugenol mentioned as starting material, are sugars, such as D-glucose, polyols, such as glycerol, and other alcohols, such as ethanol, as well as any carbon sources stated in the description of the strain.

Examples of inorganic salts are the salts of calcium, magnesium, manganese, potassium, zinc, copper, iron and other metals. A particular example of an anion of the salts is the phosphate ion. If necessary, growth factors, e.g. biotin, may be added to the nutrient medium. The ratio of the stated nutrients in the mixture depends on the type of fermentation and is established for each specific case.

In general, suitable n-eugenol concentrations for carrying out the novel process are from about 0.5 to 100, preferably from about 0.5 to 50 g/l.

The cultivation conditions are laid down so that the best possible yields are achieved. Preferred cultivation temperatures are from 24° to 32° C. The pH is preferably kept at 5-9, particularly preferably 6-8. In general, an incubation period of 15-100 hours is sufficient. During this time, the maximum amount of the desired product accumulates in the medium.

The required amount of n-eugenol can be added to the nutrient medium all at once at the beginning or in several portions during cultivation.

Apart from the above incubation of the novel microorganism, the novel process can also be used to bring the cells of the microorganism, i.e. quiescent cells which are not growing, into direct contact with the substrate n-eugenol mentioned as the starting material. In this case, the physical conditions, such as temperature, pH, aeration, etc., are chosen to be similar to those stated above.

The use of active carbon or divinylbenzyl-crosslinked polystyrene as an absorbent for the n-eugenol used is advantageous because it protects the microorganisms from the bactericidal action of the n-eugenol. Thus, the n-eugenol can be used in higher concentration.

The product coniferylaldehyde which is formed, and precipitated in the medium, can be isolated and purified by conventional methods. To isolate the product, the crystals formed can be separated off by centrifuging or filtration. These crude crystals can be purified by recrystallization or by extraction with a conventional solvent, such as methyl tert.-butyl ether. The extract can be dried, and the coniferylaldehyde purified by recrystallization. Alternatively, the coniferylaldehyde can be separated from undesirable by-products by chromatography over a conventional chromatography column, such as a silica gel column.

The Examples which follow illustrate the invention.

Isolation of the Strain

EXAMPLE 1

An agar medium containing the following components was prepared:

| | |
|---|---|
| n-eugenol | 0.5 g/l |
| ®Amberlite XAD-2 (= divinylbenzyl-crosslinked polystyrene) | 5.0 g/l |
| Ammonium sulfate | 0.5 g/l |
| Potassium dihydrogen phosphate | 1.5 g/l |
| Dipotassium hydrogen phosphate | 3.6 g/l |
| Magnesium sulfate.7 hydrate | 0.5 g/l |
| Manganese sulfate.1 hydrate | 0.05 g/l |
| Biotin | 0.1 mg/l |
| Trace element solution | 2.0 ml/l |
| Agar | 18.0 g/l |

Sterilization was carried out at 121° C. for 15 minutes. The two phosphate salts were heat-sterilized separately from the remaining medium. The n-eugenol was not sterilized and was added at a medium temperature of 50° C. and stirred in throughly. Agar plates having a volume of 40 ml/plate were cast and, after solidifying, were each charged with 0.1 ml of different suspensions of humus-containing soil samples. These plates were incubated for 14 days at 25° C. Pale yellow colonies were removed and purified in a conventional manner.

These strains were then transferred individually into 10 ml of a sterile nutrient medium (referred to below as HE medium) which contained 0.5% of yeast extract, 0.5% of ammonium sulfate, 0.15% of potassium dihydrogen phosphate, 0.36% of dipotassium hydrogen phosphate, 0.05% of magnesium sulfate 0.7 hydrate, 0.1 mg/l of biotin, 0.2% (v/v) of trace element solution and 0.005% of manganese sulfate 0.1 hydrate.

The batches were incubated for 16 hours at 25° C. and 250 rpm. After this time, 10 ml of the same medium, but containing 0.4 g/l of n-eugenol, were added. The n-eugenol was added in the form of a 50% strength solution in N,N-dimethylformamide (DMF). After incubation for a further 24 hours, the batches were extracted with one volume of ethyl acetate. 5 μl portions of these extracts were applied individually to commercial silica gel plates and developed with a mobile phase consisting of n-butanol, 25% strength ammonia, 96% pure ethanol and water in a ratio of 120:60:30:15. After the development, the n-eugenol and its degradation products were rendered visible in an iodine chamber. The strains which completely convert n-eugenol and have the physiological and morphological properties described above belong to the species *Arthrobacter globiformis*. As stated above, a strain of this type has been deposited.

Isolation of Suitable Mutants.

EXAMPLE 2

A 100 ml flask was charged with 20 ml of sterile liquid nutrient medium as described in Example 1. This batch was inoculated with a loop of DSM 3597 from an agar plate of the same composition and was incubated overnight at 25° C. and at 250 rpm, while shaking.

A second flask containing the same composition but with the addition of 0.08 ml of a 50% strength solution of n-eugenol in dimethylformamide was inoculated with 4 ml of this preculture and likewise incubated at 25° C. and at 250 rpm, while shaking. After 4.5 hours, the conversion of the added n-eugenol was checked by means of thin layer chromatography, as described in Example 1. Experience has shown that the conversion at this time is about 50%. After 5 hours, 1.0 ml of a 5% strength MNNG solution (in dimethylformamide) was added. The culture was then shaken for a further 10 minutes. Thereafter, the total culture was centrifuged at 4° C. for 10 minutes while maintaining sterile conditions, and the supernatant liquid was discarded. The cells removed by centrifuging were taken up in 10 ml of an aqueous solution which contained 10% of glycerol and 5% of lactose. This suspension was frozen at −85° C. until use. The living cell count for this suspension was carried out in a conventional manner. A suspension of the thawed cells which contained 100 viable cells per 0.1 ml was then prepared. 0.1 ml portions of this suspension were then plated out on 100 glycerol minimal medium plates and incubated for 4 days at 25° C. These were transferred in a conventional manner with velvet-covered rods onto a n-eugenol-containing nutrient agar, as described in Example 1. These plates were incubated for 2 days at 25° C. Colonies which showed good growth on the glycerol minimal medium and poor growth or no growth at all on the n-eugenol medium were isolated. These clones were then tested in liquid culture, as described in Example 1. Batches which had a fluorescent yellow color after incubation for a total of 40 hours were investigated by thin layer chromatography. Authentic coniferylaldehyde was used for this purpose as a reference. Clones which converted the n-eugenol used exclusively to coniferylaldehyde under these conditions were isolated, and preserved in a conventional manner.

Conversion of n-eugenol

EXAMPLE 3

A 1 liter fermenter was charged with 900 ml of a sterile medium which contained the following components: 2.0 g of glycerol, 1.0 g of ammonium sulfate, 1.5 g of potassium dihydrogen phosphate, 3.6 g of dipotassium hydrogen phosphate, 0.5 g of magnesium sulfate 0.7 hydrate, 0.05 g of manganese sulfate 0.1 hydrate, 2 ml of trace element solution and 0.1 mg of biotin.

A 100 ml preculture consisting of the same medium was incubated with a mutant of *Arthrobacter globiformis* (cf. Example 2) for 16 hours at 25° C. and at 250 rpm. The 1 liter fermenter was inoculated with this preculture and operated at 25° C. and 500 rpm and with 0.2 part by volume of air per part by volume of fermentation solution per minute. 4 hours after inoculation, 0.4 ml of n-eugenol (50% strength in dimethylformamide) was added. The degradation of the n-eugenol was monitored by thin layer chromatography (cf. Example 1). After a further 2 hours and 6 hours, another 0.4 ml of n-eugenol solution was added.

The fermentation was terminated when the n-eugenol had been converted. The total batch was extracted three times with methyl tert.-butyl ether. The extracts were dried, and the residue taken up in 50 ml of acetonitrile. The concentration of the coniferylaldehyde formed was determined in a conventional manner by HPLC. It was found to be 185 mg/l, based on the original fermentation medium, corresponding to a yield of 44%, based on the n-eugenol used.

EXAMPLE 4

In a fermenter, 800 ml of a sterile nutrient medium containing the following components were prepared: 5 g of yeast extract, 5 g of ammonium sulfate, 0.5 g of magnesium sulfate 0.7 hydrate, 0.05 g of manganese sulfate. 1 hydrate, 0.1 mg of biotin, 1.5 g of potassium dihydrogen phosphate, 3.6 g of dipotassium hydrogen phosphate, 2 ml of trace element solution and 20 g of active carbon powder.

A 200 ml preculture of a mutant obtained as described in Example 2 was prepared in the same medium, which in this case did not contain any active carbon. Inoculation was effected by means of a loop of cells. Incubation was carried out at 25° C. and at 250 rpm, while shaking.

Before the fermenter was inoculated, 2 g of n-eugenol were added and stirred in for 10 minutes. The fermenter was inoculated with the preculture. Incubation was carried out at 25° C., at 500 rpm and at an aeration rate of 0.2 part by volume of air per part by volume of fermentation per minute for 28 hours. The conversion was checked in a conventional manner by means of thin layer chromatography. After the n-eugenol had been completely converted, the 50 ml sample was extracted with methylene chloride until the aqueous, active carbon-containing phase no longer contained any coniferylaldehyde. The combined extracts were evaporated to dryness. The residue was dissolved in 50 ml of water, and the solution was analyzed by means of HPLC. The yield of coniferylaldehyde was 1.25 g/l (65%), based on the original fermentation broth.

EXAMPLE 5

The conversion was carried out similarly to Example 4. Instead of the active carbon, however, 20 g of ®Amberlite XAD-2 and 2 g of n-eugenol (in 100 ml of distilled water) were added to the fermentation medium after a fermentation time of 8 hours. The yield was 750 mg/l (40%).

Isolation of the Coniferylaldehyde

EXAMPLE 6

The fermentation broths obtained as described in Examples 3-5 were extracted by shaking with methyl tert.-butyl ether until coniferylaldehyde could no longer be detected in the aqueous phase. The combined extracts were evaporated down in a rotary evaporater at 40° C. The residue was dissolved in 100 ml of methyl tert.-butyl ether, and the solution was clarified by filtration. 200 ml of n-heptane were added to the filtrate, and the mixture was evaporated down to 150 ml in a rotary evaporater at 40° C. The coniferylaldehyde crystallized out under these conditions. It was recrystallized twice from boiling n-hexane. Pale yellow needles of melting point 84° C. were obtained.

We claim:

1. *Arthrobacter globiformis* DSM 3597 and its mutants which convert n-eugenol to coniferylaldehyde without further changing the coniferaldehyde.

* * * * *